United States Patent [19]

Corso et al.

[11] 4,379,937

[45] Apr. 12, 1983

[54] SELECTIVE ACYLATION OF HYDROXY-AMINO-ARYLSULFONIC ACIDS

[75] Inventors: Anthony J. Corso, Coventry; Kathleen M. Colavito, Warwick; Thomas S. Phillips, East Greenwich, all of R.I.

[73] Assignee: American Hoechst Corporation, Somerville, N.J.

[21] Appl. No.: 304,748

[22] Filed: Sep. 23, 1981

[51] Int. Cl.$^3$ .................. C07D 215/16; C07C 143/42

[52] U.S. Cl. ................................ 546/155; 260/507 R; 260/465 D; 546/288; 546/294; 546/295

[58] Field of Search ........................ 260/507 R, 465 D; 546/294, 295, 155, 288; 560/10, 12, 13

[56] References Cited

U.S. PATENT DOCUMENTS 2,335,237 11/1943 Coneetti ................................ 560/12
3,232,980 2/1966 Shultis, Jr. et al. ............ 260/507 R

FOREIGN PATENT DOCUMENTS 816991 7/1959 United Kingdom .

OTHER PUBLICATIONS

Donaldson, *The Chemistry and Technology of Naphthalene Compounds*, pp. 332, 334 (1958).

*Primary Examiner*—Nicky Chan
*Attorney, Agent, or Firm*—Stephan P. Williams

[57] ABSTRACT

An improved process for selectively N-acylating hydroxy-amino-arylsulfonic acids is disclosed wherein the hydroxy-amino-arylsulfonic acid is dissolved in water by treatment with an alkaline lithium salt, such as lithium hydroxide, and the acylation is conducted while maintaining the pH at about 3–6. The N-acyl-hydroxy-amino-arylsulfonic acids are useful as dyestuff precursors.

15 Claims, No Drawings

SELECTIVE ACYLATION OF HYDROXY-AMINO-ARYLSULFONIC ACIDS

BACKGROUND OF THE INVENTION

The present invention relates to an improved process for acylating hydroxy-amino-organosulfonic acids, particularly hydroxy-amino-arylsulfonic acids.

The N-acyl-hydroxy-amino-arylsulfonic acids are wellknown intermediates in the preparation of water soluble dyestuffs. For example, the acylated "letter" acids, such as acetyl H-acid (8-acetylamino-1-naphthol-3,6-disulfonic acid) and benzoyl K-acid (8-benzoylamino-1-naphthol-3,5-disulfonic acid) are standard couplers for water soluble azo dyestuffs.

The traditional method for acylating hydroxy-amino-arylsulfonic acids to obtain the N-acyl derivative involves four procedural steps:

(1) dissolving the reactant in aqueous solution by neutralization with sodium hydroxide or sodium carbonate;

(2) acylating with an anhydride or acyl halide at about neutral to moderately alkaline pH;

(3) saponifying the acylated hydroxy group by alkalization and heating; and (4) isolating the N-acylated product by acidification of the reaction mixture to cause precipitation (salt added as needed to effect complete precipitation) followed by filtration.

This method has a number of disadvantages associated with it because of the oxygen acylation which competes with the desired nitrogen acylation. Excess acylating agent must be employed to drive the reaction to completion. The ester formed by acylation of the hydroxy group must be saponified which increases production time and consumes energy because of the heating required. The acid formed by saponification tends to show up in the final product. The product must be isolated by precipitation in most cases since the reaction solution contains too much salt to be practical as a dyestuff precursor. This precipitation increases production time and causes reduced yield of product since some product is lost to the mother liquor (75–85% yield is typical), and the mother liquor must be treated biologically since it contains product, salts and organic acid.

SUMMARY OF THE INVENTION

Applicant has discovered an improved method for selectively N-acylating hydroxy-amino-arylsulfonic acids which results in higher yield of product, higher product purity, shorter production time, less energy and reactant consumption, lower salt content in product, and no waste water. Moreover, applicant's method makes it possible to isolate the product directly as an aqueous solution suitable for use as a dyestuff precursor without further purification, or to isolate the product by spray drying.

Applicant's method comprises dissolving the hydroxy-amino-arylsulfonic acid in water by treatment with an alkaline lithium salt such as lithium hydroxide or lithium carbonate, followed by acylating while maintaining the pH at about 3–6.

DETAILED DESCRIPTION OF THE INVENTION

According to the present invention, hydroxy-amino-arylsulfonic acids may be selectively N-acylated by forming a lithium salt of said acid in water, generally at a pH less than 7, followed by acylation with a conventional acylating agent while maintaining the pH at about 3–6.

The hydroxy-amino-arylsulfonic acids which may be acylated according to the present invention may be any of the known aromatic sulfonic acids bearing at least one hydroxy group and at least one amino group on the aromatic ring. These aromatic sulfonic acids may, of course, also contain other substituents which do not interfere with the acylation reaction.

Thus, typical aromatic sulfonic acids have the general formula:

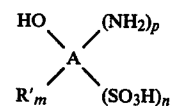

wherein A represents an aromatic ring system, preferably benzene, naphthalene, pyridine or quinoline, R' represents a substituent which does not interfere with the acylation reaction and may be the same or different if m is greater than 1, and is preferably halo, lower alkyl, lower alkoxy, hydroxy, phenyl, nitro, cyano, carboxy, lower alkylamino, or lower alkyl or phenyl substituted by one or more of these substituents; m is an integer from 0–4, preferably 0, n is an integer from 1–4, preferably 1–2, and p is an integer from 1–2, preferably 1.

The acylating agent which may be employed in the present process may be any of those currently utilized to acylate aromatic amines. Typical acylating agents are the anhydrides and acid halides of organic acids such as, for example, compounds of the formula:

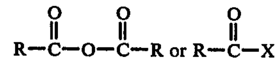

wherein X is halogen, preferably chlorine or bromine, and R is alkyl, aryl, or substituted alkyl or aryl. Preferably R is lower alkyl of 1–6 carbon atoms, phenyl, or substituted lower alkyl or phenyl wherein the substituents may be one or more of halo, nitro, lower alkoxy, phenoxy, lower alkyl (if substituted phenyl), phenyl (if substituted alkyl) and combinations thereof. Most preferred are acetic anhydride and benzoyl chloride.

The alkaline lithium salts which may be utilized to solubilize the hydroxy-amino-arylsulfonic acids and to maintain the mildly acidic pH during the acylation reaction may be any of those lithium salts of weak acids which are at least slightly water soluble, and thus provide an alkaline pH. Typical of these are lithium hydroxide, lithium carbonate, lithium bicarbonate, lithium formate, lithium acetate, lithium oxalate, lithium citrate, lithium benzoate, and lithium salicylate. Most preferred is lithium hydroxide.

In practicing the present invention, the hydroxy-amino-arylsulfonic acid (substrate) is slurried in water and treated with an alkaline lithium salt, such as lithium hydroxide, until solution of the substrate as a lithium salt occurs, generally at a pH of about 3–6. This solution of the lithium salt of the substrate is then treated with from about 1–2, preferably about 1–1.3, equivalents of acylating agent while maintaining the pH at about 3–6, preferably about 3–5, with additional alkaline lithium salt. Under these mildly acidic conditions, the reaction is essentially selective to N-acylation.

The solution of N-acylated substrate may be utilized directly as a dyestuff intermediate in liquid form, or it may be dried, such as by spray drying, to give a powder of about 60–85% strength (the remainder being salt and minor amounts of impurities). Precipitation of the product from the solution in which it is prepared is not required, as is done in the traditional process, because the salt content of the solution is within commercially acceptable levels. Yields of N-acylated substrate generally exceed 95% under the present process.

The invention may be described in greater detail by the following examples in which the parts and percentages are by weight. Although phrased in the present tense, these are actual working examples.

EXAMPLE 1

Benzoyl H-Acid

A reaction flask is charged with 400 g of water and 82.4 g H-acid (8-amino-1-naphthol-3,6-disulfonic acid, 82.8%, 0.2 moles). Lithium hydroxide monohydrate ($LiOH.H_2O$) is added over thirty minutes until a clear solution having pH 5.5 results. Over a period of one hour 35.5 g of benzoyl chloride are added while maintaining the pH at about 4–5 with $LiOH.H_2O$. This solution is stirred for an additional two hours to stabilize the pH, which is adjusted as necessary to 4–5 with $LiOH.H_2O$ (total usage of $LiOH.H_2O$ is 21 g to this point). This solution is acidified to pH 3.0 with 1.5 ml of 96% $H_2SO_4$ and filtered to remove benzoic acid and other insoluble impurities, yielding 597 g of solution which contains 13.5% benzoyl H-acid (yield 95%). Drying this solution yielded a powder of 73.2% assay based on a reference sample of commercial benzoyl H-acid of 63.6% assay.

EXAMPLE 2

Benzoyl K-Acid

A reaction flask is charged with 400 g of water and 71.4 g K-acid (8-amino-1-naphthol-3,5-disulfonic acid, 89.3%, 0.2 mole). The pH is raised to 5.0 with $LiOH.H_2O$ and the solution cooled to 15° C. Over a two hour period, 28 g of benzoyl chloride are added while maintaining the pH at 4.5–5.0 with $LiOH.H_2O$. This solution is stirred an additional two hours with the pH adjusted as necessary to 4.5–5.0. An additional 8.4 g of benzoyl chloride are added over one and one-half hours while maintaining the pH with $LiOH.H_2O$ (about 25 g total added to this point). This solution is dried to yield 121.8 g of powder containing 71.1% benzoyl K-acid. The yield was 102% based on a reference sample of commercial benzoyl K-acid of 62.9% assay.

COMPARATIVE EXAMPLES

A. Benzoyl H-Acid

A reaction flask is charged with 86 g of water, 78.03 g H-acid (87.4%, 0.2 moles), and 22 mls of 40% NaOH and heated to 45° C. At this temperature a solution of 23 g of $Na_2CO_3$ in 210 g of water is added, and the solution cooled to 20° C. Over a three hour period 31.2 g of benzoyl chloride are added followed by 18 ml of 40% NaOH, then over 35 minutes 5.6 g benzoyl chloride are added and the solution stirred for an additional two hours. The pH is adjusted from 9.5 to 11.5 with about 20 ml of 40% NaOH and heated to 80° C. for two hours to hydrolyze O-acylated material. At this point the benzoyl H-acid produced has a strength of 46.1% on a dried down basis which is too weak for general commercial use. In order to increase the product strength it is precipitated from solution by cooling to 30° C., lowering the pH to 4.0 with about 35.0 g of 96% $H_2SO_4$, and stirring overnight. After filtering, the filtercake is dried to give 113.9 g of powder containing 60.6% benzoyl H-acid. The yield was calculated at 81.6% based on a reference sample of commercial benzoyl H-acid of 63.6% assay.

B. Benzoyl K-Acid

A reaction flask is charged with 600 g of water and 71.40 g of K-acid (89.3%, 0.20 mole) and the pH adjusted to 7.3 with 17.0 g of 50% NaOH. Over a one hour period 28.0 g of benzoyl chloride (0.20 mole) are added while maintaining the pH at 7.0–7.5 with 22.0 g $Na_2CO_3$. After stirring for one hour the pH is adjusted to 8.5–9.0 with 4 g of 50% NaOH and the solution heated to 85°–90° C. while maintaining the pH at 8.5–9.0 with an additional 3 g NaOH. This temperature is held for one hour to hydrolyze O-acylated product, then the solution cooled to 30°–35° C. and tested for free amine. The pH is lowered to 7.4 with 5.0 g of 93% $H_2SO_4$ and 14.0 g of benzoyl chloride (0.10 mole) are added over one-half hour to complete the acylation. After stirring for one-half hour, the pH is raised to 9.5 with 1 g of 50% NaOH and the solution heated to 85°–90° C. for one hour at pH 8.5–9.0. After cooling to room temperature, the pH is adjusted to 2.5 with 20 g of 93% $H_2SO_4$, the solution stirred at 10°–15° C. for one hour, and the product filtered and dried to give 92.5 g powder, assay 66.2% benzoyl K-acid. The yield was calculated to be 72.4% based on a reference sample of commercial benzoyl K-acid of 62.9% assay.

The following table graphically summarizes the advantages of the present process over the traditional method:

TABLE

COMPARISON OF ACYLATION PROCEDURES

| | Ex. 1 | Ex. 2 | Ex. A | Ex. B |
|---|---|---|---|---|
| Production Time[1] | 5 hours | 7.5 hours | 27.5 hours | 9 hours |
| Yield[2] | 95% | 102% | 81.6% | 72.4% |
| Assay[2,3] | | | | |
| as isolated | 73.2% | 71.1% | 60.6% | 66.2% |
| in solution | 73.2% | 71.1% | 46.1% | 42.6% |
| Saponification Required | No | No | Yes | Yes |
| Waste Water | None | None | Requires Treatment | |

[1]This represents the time to obtain a product of suitable strength (>50%). The times given for Examples 1 and 2 are the times required to obtain the final product in solution since the strength of the product in solution, as made, is satisfactory. The times given for Examples A and B are the times required to obtain the product as a wet filtercake since isolation as such is necessary to obtain a satisfactory strength.

[2]Yield and assay percentages are not absolute, but are related to the reference sample used as a standard.

[3]Weight percentage of free acid in dried product.

EXAMPLE 3

Acetyl Gamma-Acid

A reaction flask is charged with 550 g of water and 74.1 g Gamma acid (7-amino-1-naphthol-3-sulfonic acid, 0.2 mole) and the pH adjusted to 6 with $LiOH.H_2O$. Acetic anhydride (21 g, 0.2 mole) is added over one-half hour and the solution stirred for one hour while maintaining the pH at 4–5.5 with $LiOH.H_2O$ (12 g added to this point). A solution weighing 662 g containing 8.17% acetyl Gamma-acid (dry assay 88%) is recovered after two hours, twenty minutes total reaction time. The yield was 96.3% based on a reference sample of 73.8% assay.

EXAMPLE 4

Acetyl J-Acid

A reaction flask is charged with 500 g of water and 52 g of J-acid (6-amino-1-naphthol-3-sulfonic acid, 0.2 mole). Lithium hydroxide monohydrate is added until solution occurs (about pH 7.3), then the pH adjusted to 6.5 with about 7 g of 5% HCl. Acetic anhydride (21.5 g, 0.2 mole) is added over one hour and the solution stirred for one hour while maintaining the pH at 5 to 5.5 with $LiOH.H_2O$ (16.2 g added to this point). A solution weighing 610 g containing 8.44% acetyl J-acid (90.2% yield) was recovered.

EXAMPLE 5

2-Benzoylaminophenol-4-sulfonic Acid

A reaction flask is charged with 41.0 g (0.2 mole) 2-aminophenol-4-sulfonic acid and 400 g water and the pH adjusted to 5.0 with $LiOH.H_2O$. Benzoyl chloride (31 g, 0.22 mole) is added over one hour and the solution stirred for one hour while maintaining the pH at 4–4.5 with $LiOH.H_2O$ (19.5 g added to this point). After clarification, a solution weighing 581 g containing 9.7% 2-benzoylaminophenol-4-sulfonic acid (96.3% yield) was recovered.

While the process of the present invention has been described primarily with respect to the acylation of hydroxy-amino-arylsulfonic acids, it is readily apparent that the present process has equal applicability to the acylation of any hydroxy-amino-organosulfonic acid. For example, any hydroxy-amino-aliphatic, -cycloaliphatic or -heterocyclic sulfonic acid, optionally substituted by non-interfering substituents, may be advantageously acylated following the teachings of this invention. In addition, while ordinarily the sulfonic acid to be acylated is dissolved prior to acylation, complete solution of the sulfonic acid is not necessary and it may be reacted as a slurry.

What is claimed is:

1. In a method for making an N-acylated hydroxy-amino-arylsulfonic acid which comprises dissolving said hydroxy-amino-arylsulfonic acid in aqueous solution and reacting it with an acylating agent, the improvement which comprises forming a lithium salt of said sulfonic acid in aqueous solution and conducting the acylation reaction at a pH of about 3 to 6.

2. The method of claim 1 wherein said lithium salt of said sulfonic acid is formed by treating said sulfonic acid with alkaline lithium hydroxide.

3. A method for making an N-acylated hydroxy-amino-arylsulfonic acid which comprises dissolving an hydroxy-amino-arylsulfonic acid in aqueous solution by treatment with an alkaline lithium salt to form a lithium salt of said sulfonic acid, and reacting said lithium salt of said sulfonic acid with an acylating agent while maintaining said aqueous solution at a pH of about 3 to 6.

4. The method of claim 3 wherein the hydroxy-amino-arylsulfonic acid is dissolved at a pH of about 3 to 6 and the pH is maintained during the acylation reaction by addition of an alkaline lithium salt.

5. The method of claim 4 wherein the pH is maintained during the acylation reaction at about 3 to 5.

6. The method of claim 5 wherein the alkaline lithium salt is lithium hydroxide.

7. The method of claim 4 wherein said hydroxy-amino-arylsulfonic acid has the formula:

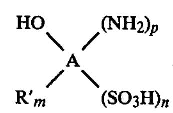

wherein A represents an aromatic ring system, R' represents a substituent which does not interfere with the acylation reaction and may be the same or different when m is greater than 1, m is an integer from 0 to 4, n is an integer from 1 to 4, and p is an integer from 1 to 2.

8. The method of claim 7 wherein A is benzene, naphthalene, pyridine or quinoline, R' is halo, loweralkyl, loweralkyoxy, hydroxy, phenyl, nitro, cyano, carboxy, loweralkylamino, or loweralkyl or phenyl substituted by one or more of these, m is 0, 1 or 2, n is 1 or 2, and p is 1.

9. The method of claim 8 wherein m is 0.

10. The method of claim 9 wherein the pH is maintained during the acylation reaction at about 3 to 5.

11. The method of claim 10 wherein the alkaline lithium salt is lithium hydroxide.

12. The method of claims 4, 7, 8, 9 or 10 wherein said acylating agent is selected from

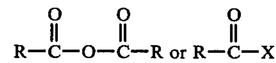

wherein X is chloro or bromo and R is loweralkyl, phenyl, or loweralkyl or phenyl substituted by one or more halo, loweralkyl, loweralkoxy, nitro, phenoxy or combinations thereof.

13. The method of claim 12 wherein said acylating agent is selected from acetic anhydride and benzoyl chloride.

14. The method of claim 12 wherein said alkaline lithium salt is lithium hydroxide.

15. The method of claim 14 wherein said acylating agent is selected from acetic anhydride and benzoyl chloride.

* * * * *

UNITED STATES PATENT AND TRADEMARK OFFICE

CERTIFICATE OF CORRECTION

PATENT NO. : 4,379,937

DATED : April 12, 1983

INVENTOR(S) : Anthony J. Corso et al.

It is certified that error appears in the above-identified patent and that said Letters Patent is hereby corrected as shown below:

Claim 2, line 3, "with alkaline lithium hydroxide" should read -- with lithium hydroxide --.

Signed and Sealed this

*Seventh* Day of *June 1983*

[SEAL]

*Attest:*

DONALD J. QUIGG

*Attesting Officer* *Acting Commissioner of Patents and Trademarks*